US009075007B2

(12) United States Patent
McKendree (10) Patent No.: US 9,075,007 B2
(45) Date of Patent: Jul. 7, 2015

(54) ACTIVE SAMPLING SMOKE SENSOR FOR THE MINING INDUSTRY

(71) Applicant: Nicholas McKendree, Princeton, WV (US)

(72) Inventor: Nicholas McKendree, Princeton, WV (US)

(73) Assignee: AMERICAN MINE RESEARCH, INC., Rocky Gap, VA (US)

( * ) Notice: Subject to any disclaimer, the term of this patent is extended or adjusted under 35 U.S.C. 154(b) by 139 days.

(21) Appl. No.: 13/828,927

(22) Filed: Mar. 14, 2013

(65) Prior Publication Data

US 2014/0160473 A1 Jun. 12, 2014

Related U.S. Application Data (60) Provisional application No. 61/797,628, filed on Dec. 12, 2012.

(51) Int. Cl.
| | | |
|---|---|---|
| *G01N 21/01* | (2006.01) | |
| *G01N 21/53* | (2006.01) | |
| *G08B 17/107* | (2006.01) | |
| *G08B 17/10* | (2006.01) | |

(52) U.S. Cl.
CPC ............ *G01N 21/532* (2013.01); *G08B 17/107* (2013.01); *G08B 17/10* (2013.01)

(58) Field of Classification Search
USPC .......................................... 356/244, 437–440
See application file for complete search history.

(56) References Cited

U.S. PATENT DOCUMENTS

| 5,247,283 | A * | 9/1993 | Kobayashi et al. ........... 340/630 |
|---|---|---|---|
| 5,420,440 | A * | 5/1995 | Ketler et al. .................. 250/573 |
| 5,610,592 | A * | 3/1997 | Okazaki ........................ 340/628 |
| 5,670,946 | A * | 9/1997 | Ellwood et al. ............... 340/628 |
| 5,926,098 | A * | 7/1999 | Wiemeyer et al. ............ 340/630 |
| 6,024,639 | A * | 2/2000 | Scherer et al. ................... 454/77 |
| 6,060,719 | A * | 5/2000 | DiTucci et al. ................ 250/554 |
| 6,107,925 | A * | 8/2000 | Wong ............................. 340/628 |
| 6,876,305 | B2 * | 4/2005 | Kadwell et al. ............... 340/630 |
| 6,920,874 | B1 * | 7/2005 | Siegel ........................ 126/299 R |
| 7,167,099 | B2 * | 1/2007 | Kadwell et al. ............... 340/630 |
| 7,417,553 | B2 * | 8/2008 | Young ........................... 340/628 |
| 7,504,962 | B2 * | 3/2009 | Smith ...................... 340/693.11 |
| 7,834,773 | B2 * | 11/2010 | Kato .............................. 340/630 |
| 2005/0224069 | A1* | 10/2005 | Patil et al. .................. 126/299 D |
| 2006/0042205 | A1* | 3/2006 | Kalous et al. ................ 55/385.1 |
| 2007/0181000 | A1* | 8/2007 | Wilson et al. ................... 96/134 |
| 2008/0286163 | A1* | 11/2008 | Garfield et al. ............... 422/120 |
| 2010/0091500 | A1* | 4/2010 | Herbst ........................... 362/294 |
| 2010/0125949 | A1* | 5/2010 | Stebbing ........................... 5/423 |
| 2010/0144261 | A1* | 6/2010 | Barkic et al. .................... 454/75 |
| 2010/0274395 | A1* | 10/2010 | Durham, III .................. 700/276 |
| 2010/0291850 | A1* | 11/2010 | Sabbaghian et al. ............ 454/61 |
| 2010/0318230 | A1* | 12/2010 | Liu ................................ 700/282 |

\* cited by examiner

*Primary Examiner* — Roy M Punnoose
(74) *Attorney, Agent, or Firm* — Harness, Dickey & Pierce, P.L.C.

(57) ABSTRACT

An optical smoke detector designed for the mining industry that includes an active sampling component and a unique air flow system to reduce the environmental impact of underground mining. The active sampling smoke detector may include an intake fan, an optical sensing unit, an air path between the intake fan and the optical sensing unit, and a controller operatively connected to the intake fan and the optical sensing unit, the controller being configured to regulate fan speed and output at least one signal indicative of air quality passing through the optical sensing unit.

17 Claims, 8 Drawing Sheets

ACTIVE SAMPLING SMOKE SENSOR FOR THE MINING INDUSTRY

PRIORITY STATEMENT

This application claims the benefit of U.S. Provisional Application No. 61/797,628, filed on Dec. 12, 2012. The disclosure of the above application is incorporated herein by reference.

FIELD

Example embodiments relate generally to smoke detectors for the mining industry and more specifically to smoke detectors for underground mining where environmental factors such as air quality limit the operation of smoke sensors.

BACKGROUND

Fire detection in certain industries and especially in mining is known to be difficult due to the amount of dust and/or particulate matter suspended in the air. As such, traditional smoke detection devices cannot be used in such environments because the dust and/or suspended particulate matter is misinterpreted as smoke caused by a fire which often results in false alarms. Additional problems with such known detection devices include clogging of the detection devices with dust with that inhibits proper sensor function.

Known carbon monoxide sensors may be useful for detection of the combustion of certain materials, such as coal and wood. However, smoke monitoring remains necessary to detect fires with low heat and low output of carbon monoxide. For example, in many industries using heavy equipment, certain events may produce thick smoke while there is in fact no actual event that would result in the activation of a conventional temperature or carbon monoxide sensor and alarm. Moreover, certain gases are known to interfere with carbon monoxide sensors which limit or otherwise eliminate the use of such sensors in many applications.

Due to the limitations of the above devices, it is known to use optical obscuration smoke detectors in a particularly dusty or dirty environment where there may be smoke without heat or fire, such as an underground mine including coal mines. However, these reflected light-type devices are known to have difficulty correlating sensor output with the percent of obscuration of a light beam. For example, an amount of light reflected from smoke of a given light obscuration level may be dependent on the color of the smoke, particle size and distribution, degree of turbulence within the optical chamber of the device, etc. Therefore, it is difficult with known optical smoke detectors to make an accurate correlation of the amount of smoke and an actual fire, if not impossible.

U.S. Pat. No. 5,420,440 relates to an optical obscuration smoke detector that uses a horizontal air shunt to capture air flow. The downfall of this design is due to the reliance of the device on an environmentally dependent air flow (i.e., ambient air movement). The reliance on ambient air movement through the detection device in a location with low air flow, such as in a mine, may result in ineffective detection of smoke due to an inconsistent flow of air/smoke through its optical detector. Therefore, the device would have difficulty correlating sensor output with the percent of obscuration of a light beam.

SUMMARY

The subject matter of the present specification relates to an active sampling smoke detector that incorporates a unique air path that eliminates a large percentage of environmental contaminates and controls the quality and quantity of air being sampled.

The active sampling smoke detector is designed to detect smoke in dusty conditions, such as in a mine, and may include an intake fan, an optical sensing unit, an air path between the intake fan and the optical sensing unit, and a controller operatively connected to the intake fan and the optical sensing unit, the controller being configured to regulate fan speed and output at least one signal indicative of air quality passing through the optical sensing unit.

The air path active sampling smoke detector may have a substantially u-shape. A first end of the air path communicates with an environment outside of the smoke detector and a second end of the air path terminates at a closable access port in a housing of the smoke detector. A reducing element in the air path between the intake fan and the optical sensing unit is configured to inhibit entry of certain particulate matter from the optical sensing unit.

The active sampling smoke detector may also include a dust collection chamber in the air path between the optical sensing unit and an access port in a housing of the smoke detector and have an exhaust hood in a housing of the smoke detector. The exhaust hood funnels exhaust air from the optical sensing unit outside of the housing to prevent contamination of the smoke detector from the surrounding environment.

The optical sensing unit may have two detectors and a light source. A first detector is situated in line with the light source to provide an obscuration measurement of air flowing through the optical sensing unit and a second detector is situated perpendicular to the light source to provide a reflection measurement. The two detectors are configured to detect reflection of light off of particles in the air path that are 90 degrees to the light source and obscuration of light from the particles that are 180 degrees to the light source. The optical chamber module may also have an optical filter configured to reduce an intensity of light received by at least one of the detectors.

The optical chamber module includes an air reducing path configured to prevent smoke in the air path from traveling above or below a light path between the light source and at least one of the detectors.

BRIEF DESCRIPTION OF THE DRAWINGS

One or more example embodiments of the invention described herein are explained in more detail below on the basis of the drawings, in which.

DETAILED DESCRIPTION OF THE EXAMPLE EMBODIMENTS

Various example embodiments will now be described more fully with reference to the accompanying drawings in which some example embodiments are shown.

Detailed illustrative embodiments are disclosed herein. However, specific structural and functional details disclosed herein are merely representative for purposes of describing example embodiments. This invention may, however, be embodied in many alternate forms and should not be construed as limited to only the embodiments set forth herein.

Accordingly, while example embodiments are capable of various modifications and alternative forms, the embodiments are shown by way of example in the drawings and will be described herein in detail. It should be understood, however, that there is no intent to limit example embodiments to the particular forms disclosed. On the contrary, example embodiments are to cover all modifications, equivalents, and alternatives falling within the scope of this disclosure. Like numbers refer to like elements throughout the description of the figures.

Although the terms first, second, etc. may be used herein to describe various elements, these elements should not be limited by these terms. These terms are only used to distinguish one element from another. For example, a first element could be termed a second element, and similarly, a second element could be termed a first element, without departing from the scope of this disclosure. As used herein, the term "and/or," includes any and all combinations of one or more of the associated listed items.

When an element is referred to as being "connected," or "coupled," to another element, it can be directly connected or coupled to the other element or intervening elements may be present. By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Specific details are provided in the following description to provide a thorough understanding of example embodiments. However, it will be understood by one of ordinary skill in the art that example embodiments may be practiced without these specific details. For example, systems may be shown in block diagrams so as not to obscure the example embodiments in unnecessary detail. In other instances, well-known processes, structures and techniques may be shown without unnecessary detail in order to avoid obscuring example embodiments.

Although a flow chart may describe the operations as a sequential process, many of the operations may be performed in parallel, concurrently or simultaneously. In addition, the order of the operations may be re-arranged. A process may be terminated when its operations are completed, but may also have additional steps not included in the figures. A process may correspond to a method, function, procedure, subroutine, subprogram, etc. When a process corresponds to a function, its termination may correspond to a return of the function to the calling function or the main function.

As disclosed herein, the term "storage medium" or "computer readable storage medium" may represent one or more devices for storing data, including read only memory (ROM), random access memory (RAM), magnetic RAM, core memory, magnetic disk storage mediums, optical storage mediums, flash memory devices and/or other tangible machine readable mediums for storing information. The term "computer-readable medium" may include, but is not limited to, portable or fixed storage devices, optical storage devices, and various other mediums capable of storing, containing or carrying instruction(s) and/or data.

Furthermore, example embodiments may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a computer readable storage medium. When implemented in software, a processor or processors will perform the necessary tasks.

In an example embodiment, the subject matter described herein relates to a smoke sensing device that includes designs that allow the device to be used in underground mines where the surrounding environment would cause traditional smoke sensors to malfunction.

Figure 1:
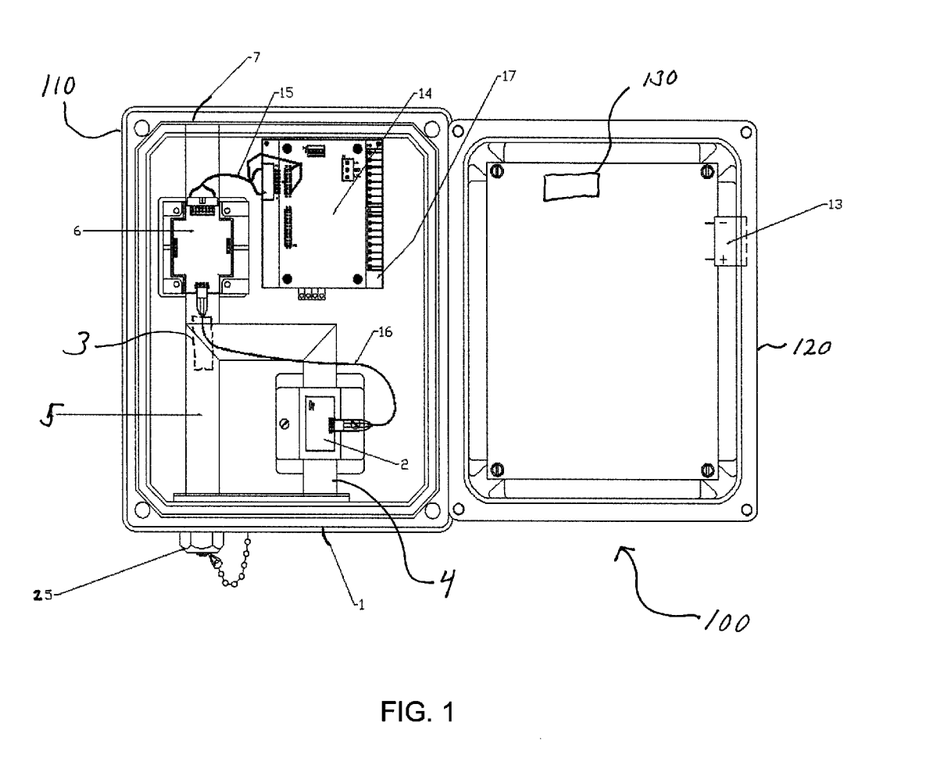
FIG. 1 shows an example embodiment of an active sampling smoke detector.

Referring now to an example embodiment shown in FIG. 1, there is shown an active sampling smoke sensor 100 having a housing 110. Stored within the housing 110 is an engineered air path 4 connected to an intake fan module 2. The intake fan module 2 draws air into the sensor 100 through an air intake port 1 that is open to the exterior of the housing 110 and into the air path 4. An optical chamber module 6 is also connected to the air path 4 such that air drawn into the air path 4 via the intake fan module 2 passes into and through the optical chamber module 6. An exhaust outlet 7 that opens to the exterior of the housing 110 is connected to the optical chamber module 6 to allow air from the optical chamber module 6 to exhaust outside of the housing 110. The housing 110 may also include a port to access the dust chamber 5 to allow for access to the air path 4 and/or cleaning of the sensor 100. The housing 110 may further include a door 120 that seals and protects the sensor 100 and its component parts.

In an example embodiment, the air path 4 may have a substantially u-shaped configuration that delivers less volume of the heavier rock dust and coal dust found in the air of mines to the optical chamber module 6. For example, the u-shaped configuration causes the air and particles contained therein to encounter sudden changes in direction due to the bends in the u-shaped configuration, thereby causing the heavier particles to fall out of the air flowing through the air path 4. As shown in FIG. 1 the u-shaped configuration provides substantially 90 degree bends in the air path 4. A bend in the air path 4 at a junction of the dust chamber 5 and the optical chamber module 6 causes a sudden change in direction of the air flow such that heavier particles in the air flow will fall into the dust chamber 5.

Although the substantially 90 degree angles in the air path 4 will create a stronger change of direction for the airflow, as may be understood by one of skill in the art, the shape of the air path 4 may be altered from the substantially u-shaped path shown in the figures without departing from the intent and scope of the present application and claims. For example, the air path 4 may be changed such that turns in the air path have an angle other than the 90 degree turns as shown in FIG. 1. In an example embodiment, a 45 degree angle could be substituted if desired for improvement in manufacturing, etc. In various exemplary embodiments, the air path 4 may be constructed of plastic or metal depending on the manufacturability of the object and/or the intended environment of use.

A reducing element 3 may be placed in the air path 4 thereby further hampering the flow of rock dust or other particulate matter in the air flowing through the air path 4 from moving upward through the optical chamber module 6. In an example embodiment, the reducing element 3 may consist of a smaller opening, or narrowed section, within the air path 4. An example of a reducing element 3 is a cylindrical metal pipe having a diameter smaller than that of the air path 4. In an example embodiment, the reducing element 3 may be, but is not limited to, a pipe approximately 3" long by ¼" diameter. The restriction in the air path 4 caused by the reducing element 3 introduces a level of difficulty for the heavier particles in the air path 4 to enter the optical chamber module 6. Thus, the reducing element 3 alone, or in conjunction with the shape of the air path 4, aid in removing heavier dust particles from the air flow prior to reaching the optical detector module 6. A threaded cap 25 at one end of the air path 4 provides access to remove accumulated particles in the dust chamber 5.

Figure 2:
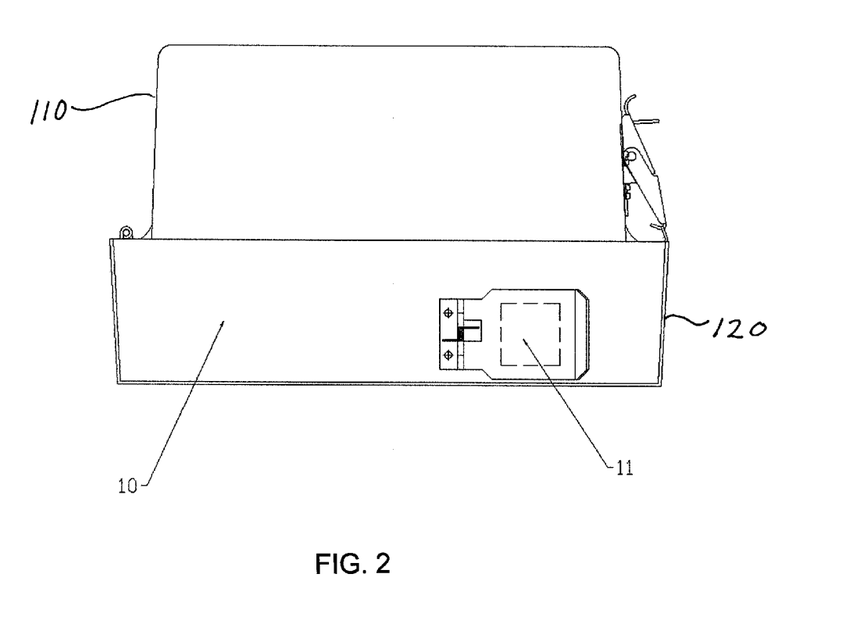
FIG. 2 shows a top view of the housing of the active sampling smoke detector of FIG. 1.

The housing 110 may also include an exhaust hood 10 (FIG. 2) at an upper exterior surface of the housing 110. In an example embodiment, the hood 10 may be attached to the door 120 of the housing 110. The hood 10 is provided to block environmental access to the interior of the sensor 100. In an example embodiment, the exhaust hood 10 also functions to funnel exhaust air from the outlet 7 to either side of the housing 110 thereby preventing contamination from the surrounding environment. Without the exhaust hood 10 installed, environmental elements would have direct access into the optical chamber module 6 and its components thereby fouling the device and disrupting the functionality of the optical chamber module 6.

The exhaust hood 10 also allows the sensor 100 to be installed without concern as to its placement relative to a fixed direction of airflow in the environment in which the sensor 100 is installed. For example, in a coal mine, there are areas that are used as air intakes and returns for ventilation purposes. In order to provide ease of installation of the sensor 100 in its environment, the exhaust of the sensor 100 is multidirectional as a result of the exhaust hood 10 and therefore, installation of the sensor 100 is not restricted to a particular location based on the ventilation plan of the mine.

In an example embodiment, the exhaust outlet 7 is located in the housing 110 at a point where the air path 4 exits into a protected area provided by the exhaust hood 10. An access port 11 or cleaning hatch in the hood (FIG. 2) is openable to allow access into the outlet 7/optical chamber module 6 for cleaning, such as with compressed air or brush.

In operation, air from the surrounding environment will be drawn into the sensor 100 through the intake port 1 by the fan module 2. The drawn-in air will travel along the air path 4 while heavier dust particles are separated out by the turns in the u-shaped air path 4 and the reducing element 3. The heavier particles will fall to the bottom of the air path 4 and into the dust chamber 5 below the reducing element 3 after passing through the u-shaped portions of the air path 4. To lessen the chances of dust entering the optical chamber module 6, the reducing element 3 provides reduced volume for airflow into the optical chamber module 6. The dust particles that are separated from the flowing air will collect in the dust collection chamber 5 section of the air path 4 above the collection cap 25. The dust collection chamber 5 can be accessed to remove accumulated dust by removal of the access cap 25. The air flowing through the air path 4 is forced through the narrowed path of the reducing element 3. The air then flows through the optical chamber module 6 for sampling and finally out the exhaust port 7 into the hood 10 to pass into the environment to the sides of the housing 100 as directed by the installed hood 10.

Figure 7:
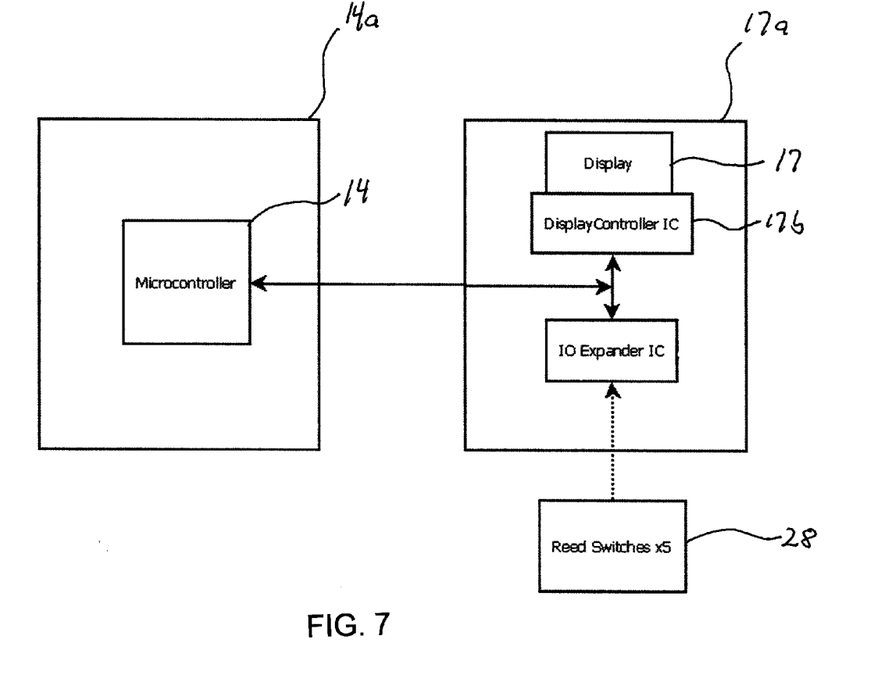
FIG. 7 shows a schematic view of an example embodiment of a microcontroller and display device of the active sampling smoke detector of FIG. 1.

Referring again to FIG. 1, the interior of the housing 110 includes the air path 4, the optical sensing chamber 6 and the fan intake module 2. The sensor 100 further includes a microprocessor board 14a having microcontroller 14 that acts as a controller and a display board 17a that includes a display 17 and a display controller 17b (FIG. 7). The microcontroller 14 may include, for example, at least one memory device (RAM, ROM), an input/output device, a processor (CPU) and a bus interconnecting the components of the microcontroller 14. Operating and processing instructions of the sensor 100 and its component parts may be stored in the at least one memory device. Also shown are the audible alarm 13, the air intake port 1, the dust chamber access cap 25, and the exhaust outlet 7.

Figure 3:
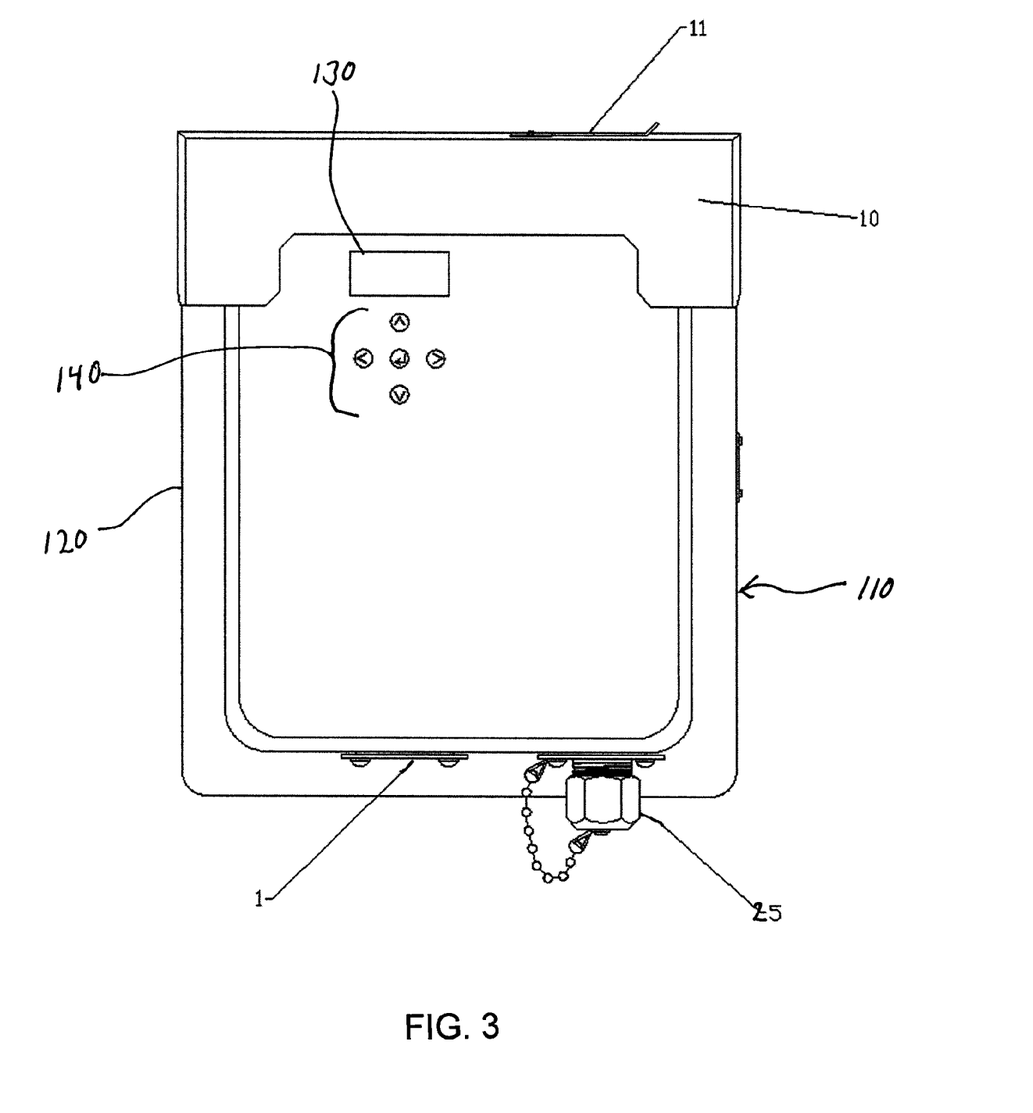
FIG. 3 is a front view of the active sampling smoke detector of FIG. 1.

FIG. 3 shows a front view of an example embodiment of the housing 110 and door 120 of the sensor 100. As shown in FIG. 3, the housing 110 may include the dust chamber access cap 25, and the air intake 1. The door 120 of the housing 110 may include the cleaning access port 11 and the exhaust hood 10 as described above. In an example, embodiment, the door 120 may further include a window 130 and a plurality of switches or buttons 140.

The "buttons" 140 and the "window" 130 shown in FIG. 3 are situated directly over the display 17 and microcontroller 14 of FIG. 1. For example, the window 130 provides viewer access to a readable display 17 on the display circuit board 17a. In an example embodiment, the window 130 may be a cut out in the door 120 and have a transparent insert provided therein, such as piece of acrylic silicone. The buttons 140 may be screen printed or labeled on the door 120 of the housing 110. Although the buttons of the example embodiment are not actual mechanical switches or buttons, use of mechanical switches or buttons, or other types of input devices is contemplated and is considered to be within the scope of the present disclosure.

In an example embodiment, the display circuit board 17a drives the display 17 having, for example, five magnetically activated reed switches 28 aligned with the five buttons 140 shown on the door 120 of the housing 110. These switches 28 provide a reliable input method and can be activated with a magnet. The buttons 140 are configured to provide input to the microcontroller 14. In an example embodiment, the button options may be UP, DOWN, RIGHT, LEFT, and ENTER. The UP/DOWN buttons will cycle between three operation modes (Clean/RUN/Test) discussed in more detail below. The RIGHT/LEFT buttons may be used to cycle between different system information, such as but not limited to temperature and communication addressing. The ENTER button can be used to silence an audible alarm of the sensor 100 for a period of time (e.g., 5 minutes).

In an example embodiment, there may be three modes on the display including 1) "clean", 2) "run" and 3) "test." In the clean mode, the display will flash "clean". The clean mode may be enabled by a user at the front panel 120 using the UP/DOWN buttons 140, for example. The sensor 100 also has the ability to track decreasing signal integrity and can indicate a clean request flag in a communications system (Modbus, other wired, wireless) to prompt the clean mode.

When the sensor 100 is in the run mode (i.e., normal operation mode) the display 14 will read the current percent obscuration detected in the optical chamber module 6 according to signals received from the optical chamber module 6 via the cable 15. When the sensor 100 is in the test mode, the display 14 will flash "test" and then the percent obscuration will be shown. The test mode is entered from the UP/DOWN buttons 140 on the cover 120 of the sensor 100. Once the sensor 100 is in the test mode the microcontroller 14 will begin to "step down" or reduce the intensity of the light source (emitter 18) until the obscuration reading reaches an alarm set point and the audible alarm 13 is triggered. Once the sensor 100 is placed back into the run mode, or times out after a period of time (minutes), then the light source intensity will return to the normal setting.

Figure 4:
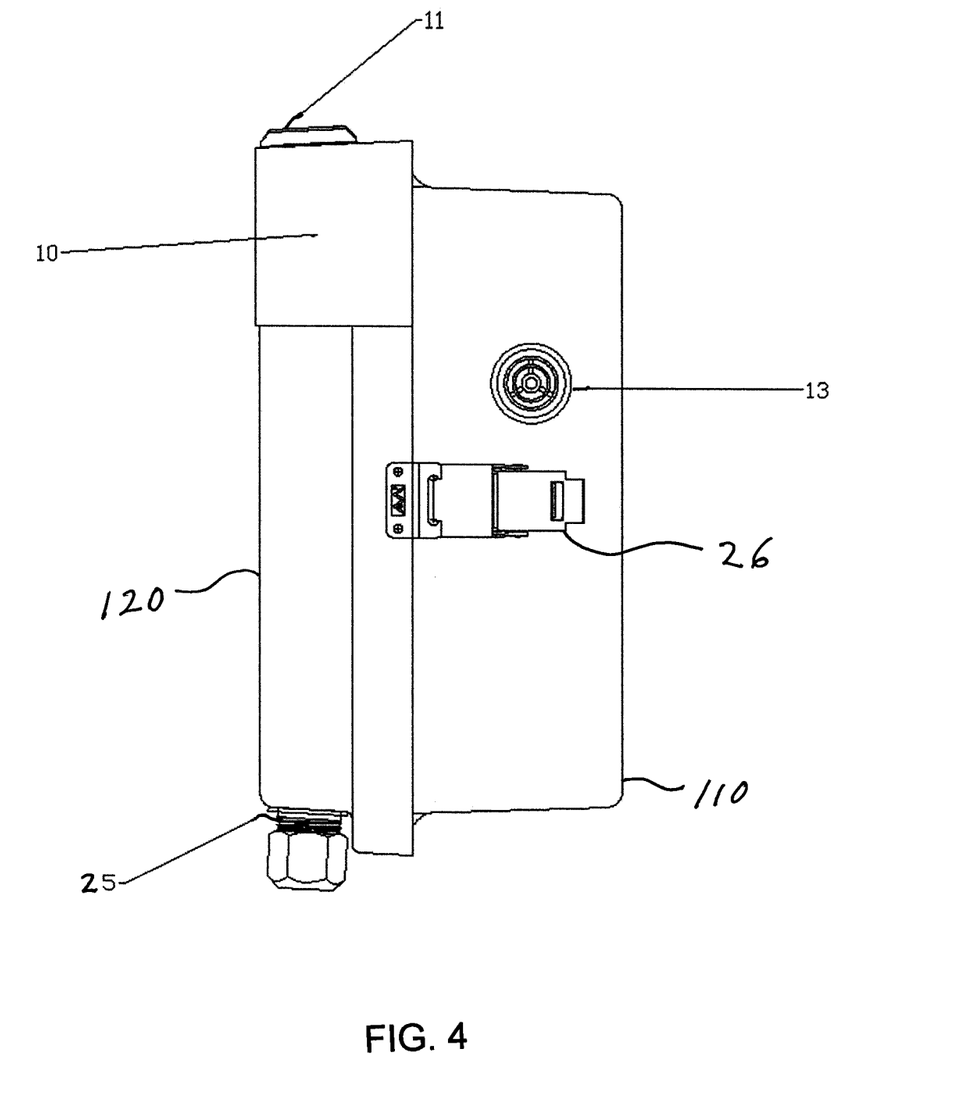
FIG. 4 is a side view of the active sampling smoke detector of FIG. 1.

FIG. 4 shows a side view of an example embodiment of the housing 110 of the sensor 100 and includes the door 120, the exhaust hood 10, access hatch 11 and the dust chamber access cap 25. As shown in FIG. 4, the housing 110 may further include a latch 26 that secures the door 120 and housing 110 as well as the audible alarm 13. The alarm 13 is operatively connected to the microcontroller 14 (FIG. 1). In an example embodiment, the alarm 13 may be a continuous buzzer alarm that is wired to an output on the display circuit board 17a that is controlled through a transistor by the microcontroller 14.

In an example embodiment, the display 17 is configured to display the percent obscuration detected by the optical chamber module 6 (described in more detail below) in accordance measurements required by the Mine Safety and Health Administration (MSHA). A connection cable 15, such as a 14-pin ribbon cable connects the microcontroller circuit board 14a to the optical chamber module 6. The cable 15 carries instruction signals from the microcontroller 14 to the optical chamber module 6 to control optical chamber module 6 and to send the readings from the optical chamber module 6 to the microcontroller 14. A control cable 16 connects the optical chamber module 6 and the fan module 2. In an example embodiment, the display board 17a is controlled by a signal from a display driver chip 17b which is communicated from the microcontroller 14 over a digital protocol, such as I2C (Inter-Integrated Circuit). The fan module 2 is controlled by an IO (Input/Output) IC on an optical chamber circuit board 150 (FIG. 5) which is controlled by the microcontroller 14 over I2C. In the embodiments shown herein, the display board 17a and the microcontroller board 14a are located over one another. For example, the microcontroller board 14a may be mounted on top of the display board 17a with standoffs separating the two boards. However, one of skill in the art would readily recognize that the boards 14a, 17a and certain other components of the sensor 100 may have other relative physical locations to one another, as well as other means of communication, without departing from the scope of the present invention.

As discussed above, the fan module 2 is used to pull environmental air into the sensor 100 that then passes through the air path 4 towards the optical chamber module 6. In an embodiment, the optical chamber module 6 and the fan module 2 are controlled by the microcontroller 14 via the cables 15 and 16 as discussed above.

In the event of a fire, smoke will be pulled into the sensor 100 and sampled. An obscuration of 2.2% per meter is the threshold set by the MSHA that requires an alarm to be sounded. In the present case, once the obscuration is measured by the optical chamber module 6 at or above the threshold of 2.2% per meter, then the microcontroller 14 will trigger the audible alarm 13 until the condition clears or a user silences the alarm using the ENTER button 140 on the cover 120.

Figure 5:
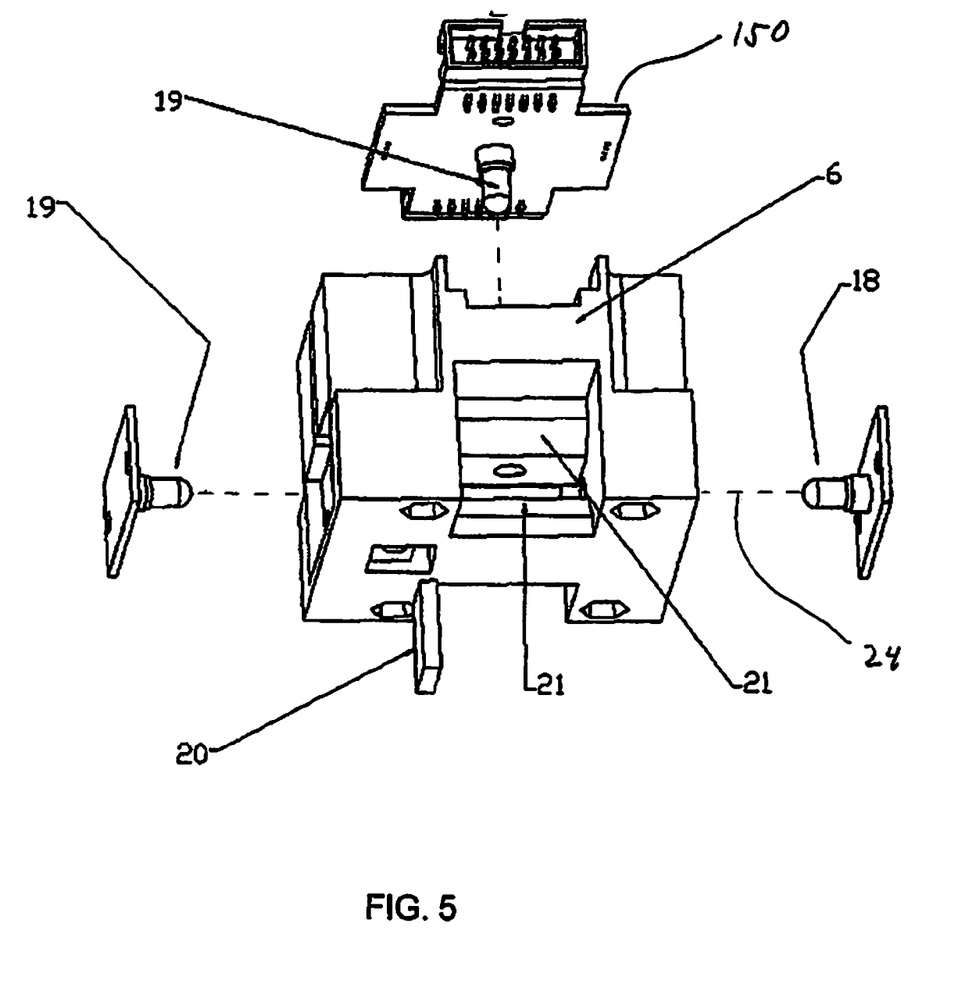
FIG. 5 shows a detailed view of an example embodiment of an optical chamber module as in FIG. 1.

FIG. 5 shows an exploded detail of the optical chamber module 6. In an example embodiment, the optical chamber module 6 includes two detectors 19 and a light source or emitter 18. In an example embodiment, the detectors 19 may be infrared phototransistors and the light source may be an infra-red light emitting diode (LED). Although infrared detectors and emitter are discussed in the example embodiment, other detectors and sensors may be used in the optical chamber module 6 without departing from the scope of the present disclosure. The optical chamber module 6 may further include an optical filter 20 and an air reducing path 21.

As shown in FIG. 5, one of the phototransistors 19 is situated in line with the light emitting diode 18 to provide an obscuration measurement of air flowing through the optical chamber module 6. A second phototransistor 19 is situated perpendicular to the light emitting diode 18 to provide a reflection measurement. The sensing elements 19 detect reflection of light off of particles (90 degrees of the emitter 18) and obscuration of light from particles (180 degrees of the emitter 18) which allows for better accuracy of detection in a dusty environment and therefore reduced false alarms. By adding the reflection sensing element 19, software stored in a storage medium, such as a memory, of the microcontroller 14 can reduce false alarms resulting from the contamination of the environment (for example rock dust) in which the sensor 100 is placed. The addition of the reflection sensor 19 provides a method to monitor for light being reflected as well as the obscuration of light. This dual sensing device and methodology reduces false alarms which can result when the obscuration level changes but the reflection level does not change due to an actual absence of smoke particles in the air. In contrast, smoke particles would cause a change in both sensors 19 (i.e., obscuration and reflection sensors). Smoke can also come from slipping or stuck belts that may not be on fire and newer belt systems do not produce carbon monoxide to set off CO sensors.

The optical filter 20 of the optical chamber module 6 may be a piece of plastic or glass that has a low light transmission property. The color of the optical filter 20 may be selected based on a particular wavelength of light that is not desired to be filtered out. For example, the optical filter may be gray to prevent filtration of light having a wavelength of approximately 850 nm (IR) but can range from 800 to 950 nm (nanometers) which is the near IR (infrared) band. The optical filter 20 in the optical chamber module 6 is configured to reduce the intensity of the emitter 18 while maintaining a useful detection sensitivity of the detectors 19. In an example embodiment, the optical filter 20 prevents an over-saturation of the sensor 19 that may result from the distance between the emitter 18 and the detectors 19 being too close.

The reducing path 21 of the optical chamber module 6 is designed so that an air path within the optical chamber module 6 is reduced by approximately 75 percent from the air path 4 outside of the optical chamber module 6 by a reduction in the diameter of the air reducing path. The reducing path 21 reduces and/or prevents smoke within the air flow being sampled from traveling above or below the light path 24 from the light emitting diode 18. For example, as dust particles in the drawn-in air come out of the u-shaped section of the air path 4 and into the reducing path 21, the sudden changes in direction cause the particles to lose velocity. The lower velocity makes it challenging for the dust to combat gravity and the resistance to flow caused by the smaller opening in the reducing path 21. Without the reducing path 21 there would be no change in the size of the path being traveled by the dust and therefore there would be little resistance to the dust (even with lower velocities).

Figure 6:
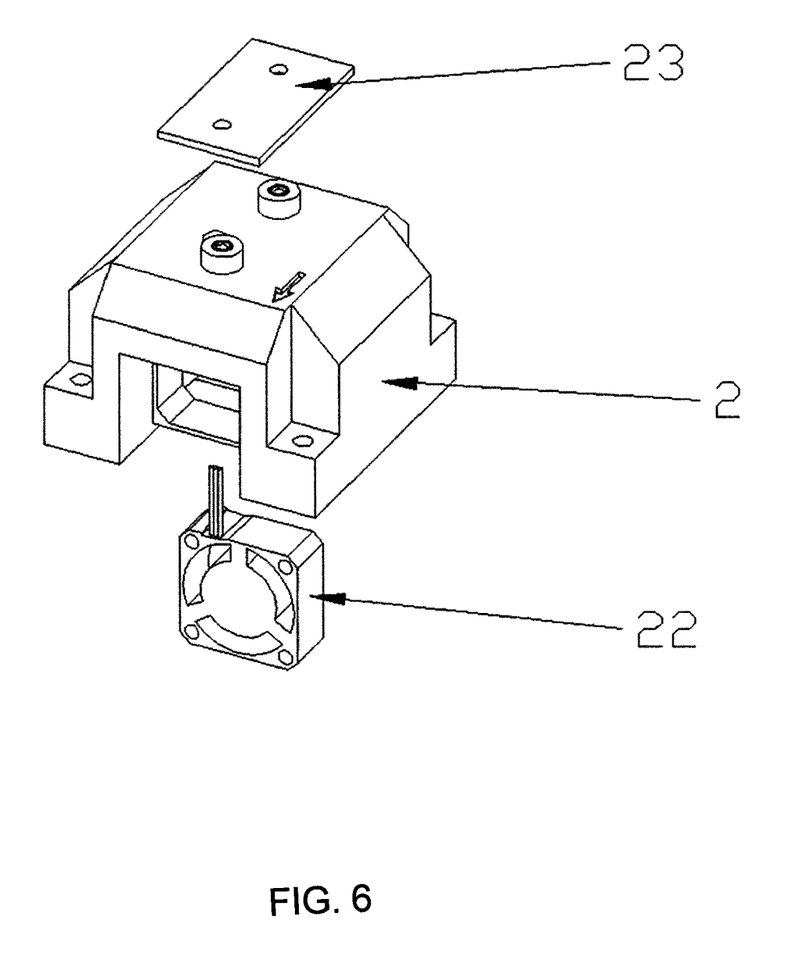
FIG. 6 shows a detailed view of an example embodiment of a fan intake module as in FIG. 1.

FIG. 6 shows an exploded detail of the fan intake module 2. In an example embodiment, the fan intake module 2 is placed in the air path 4 (FIG. 1). A fan 22 is insertable into the module 2 and is controlled by an interface circuit board 23 connected to the microcontroller 14 via cable 16 connected to the optical chamber circuit board 150. The fan module 2 provides a controlled method to actively sample the air outside of the smoke sensor 100 which makes the sensor 100 less dependent on the ambient airflow in the environment. The intake fan is controlled by a microcontroller to provide for precise control over the sampling period. In an example embodiment, the sample rate may be every 2 seconds. During the sample period, the fan 22 is activated by a signal from the microcontroller 14 for a half second to draw sample air into the sensor 100. The drawn-in air will be directed to the optical chamber module as discussed above where the optical sensors 19 will sample the air. The sample period is controlled by instructions stored in a memory of the microcontroller 14.

As the air flows through the reduced path 21, the amount of dust particles is determined by both reflection and obscuration by the arrangement of the emitter 18 and the detectors 19 in the optical chamber module 6. A signal output from the detectors 19 is sent from the circuit board 150 of the optical chamber module 6 via the cable 15 to the microcontroller 14 where the detected signal is compared to an obscuration chart stored in a memory of the microcontroller 14. The reflection component involves an observed value in that the reflection component is not directly used in a calculation but rather is indicative of a change in state (reflection or no reflection). Thus, the control software of the sensor 100 is detecting a change in the analog reading from the reflection sensor 19. The sensor 100 receives the current analog reading of the obscuration sensor 19 and the zero smoke analog reading of the reflection sensor 19 and calculates the percent obscuration.

When the detected percent obscuration is 2.2% per meter (as mandated by the MSHA), the microcontroller 14 will send a signal to enable an alarm routine that begins to toggle the audible alarm 13 indicating a fire. The microcontroller 14 can also transmit the status/state of the sensor 100 through various communication methods to a server (not shown) that may be located at a location remote from the sensor 100. For example, when the sensor 100 is located in a mine, the server may be located on the surface and provide an interface for the user to monitor the condition of the mine. In an example embodiment, while in the alarm state, the microcontroller 14 will continue to monitor for a clear condition (i.e., obscuration less that the threshold amount).

Figure 8:
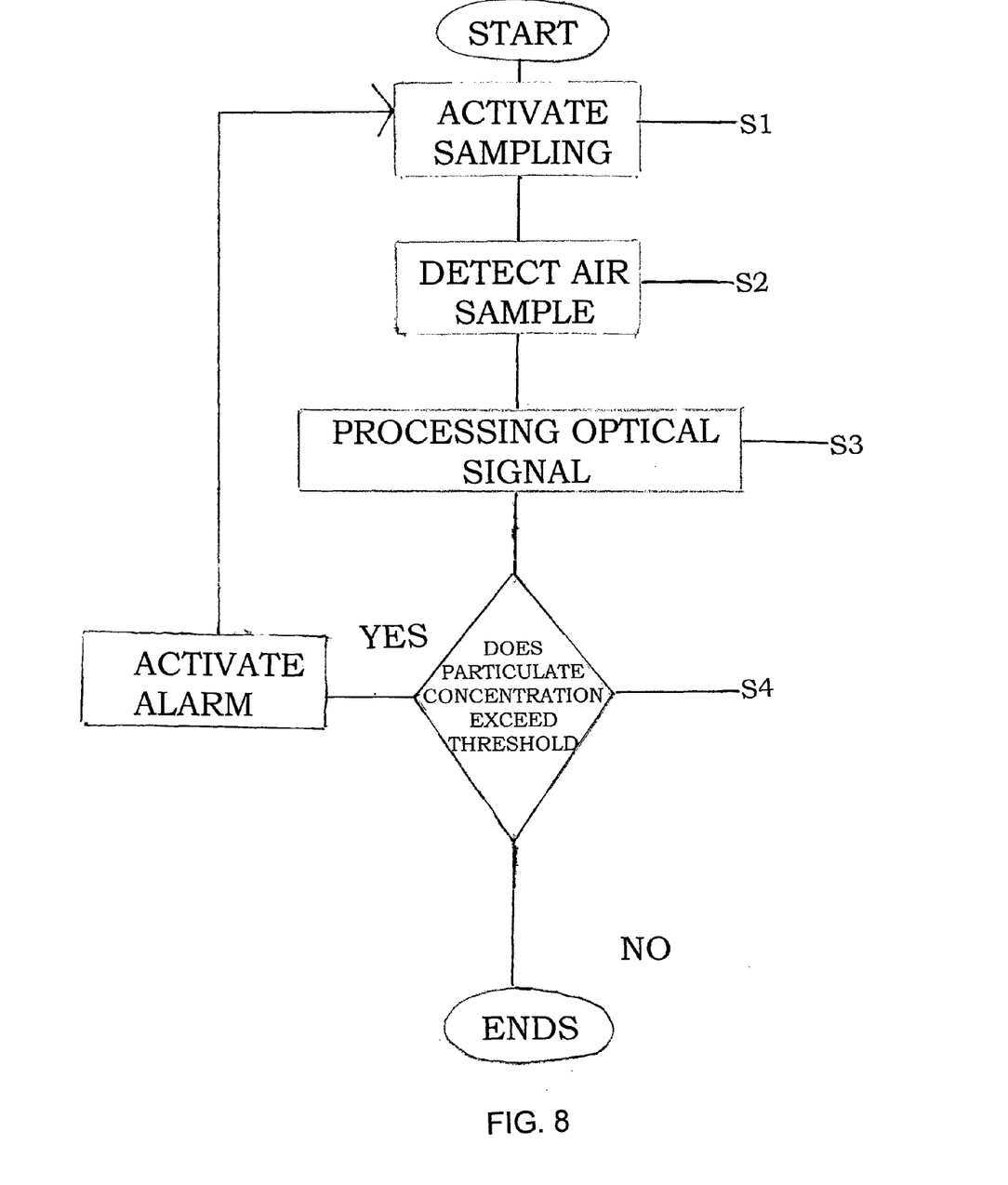
FIG. 8 shows a flowchart of an example process performed by the detector of FIG. 1.

FIG. 8 shows a flowchart of an example process performed by the sensor 100. As shown in FIG. 8, the process begins at the START and proceeds to step S1 where a preset sampling period is activated by a microcontroller. During step S1 a command signal is sent from the microcontroller to a fan module whereby a fan is activated to begin drawing air into an air path of the sensor. As discussed above, drawn-in air passes through the air path and a reducing element where larger particulates fall out of the flowing air. The process proceeds to step S2 where detection of the amount of dust or particulates are determined.

During the detection process, air passes from the air path into a reducing path in an optical chamber module. In the optical chamber module, an emitter is activated and a portion of the emitted light is detected by detectors. Particles in the air sample flowing through the optical chamber module obscure and/or reflect a portion of the emitted light. The process proceeds to step S3.

At step S3, a signal from the detectors of the optical chamber module is sent to the microcontroller where the detected signal is processed to determine the amount of obscuration of the light beam caused by dust in the air sample. The received signal is processed by the microcontroller by comparing the detected amount of obscuration with a threshold amount stored in a memory of the microcontroller. The process proceeds to step S4.

During step S4, the microcontroller determines whether a concentration of particulate matter in the air sample exceeds the threshold amount stored in a memory. If the concentration does not exceed the threshold amount (NO at step S4) the process ends. If the concentration exceeds the threshold amount (YES at step S4), the process proceeds to step S5 where an alarm is activated warning of a fire or other unsafe condition based on air quality. The process then continues to step S1 to continue air sampling.

Because the optical chamber module 6 and intake fan module 2 are designed as modules they can be easily and quickly replaced. The environment in which the sensor 100 will be used may be harsh and will often decrease the life and/or performance of these two devices. By having field replaceable modules, the entire sensor product will have a longer life. In various exemplary embodiments, the sensor 100 may include components to alarm locally or over multiple supported wired communication protocols (common to the mining industry) and/or wirelessly.

The subject matter described above presents example embodiments of an optical smoke monitor useful in mines and other environments where dusty conditions exist. While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. An active sampling smoke detector to detect for smoke in dusty conditions, comprising:
    an intake fan;
    an optical sensing unit that detects smoke particles;
    an air path between the intake fan and the optical sensing unit; and
    a controller operatively connected to the intake fan and the optical sensing unit, the controller being configured to regulate active sampling of environmental air by periodically activating the intake fan to draw an air sample into the smoke detector and output at least one signal indicative of air quality passing through the optical sensing unit.

2. The active sampling smoke detector of claim 1, wherein the air path has a substantially u-shape and a first end of the air path is in communication with an environment outside of the smoke detector and a second end of the air path terminates at a closable access port in a housing of the smoke detector.

3. The active sampling smoke detector of claim 1, further comprising an exhaust port, wherein the optical sensing unit branches from air path is contiguous with the exhaust port.

4. The active sampling smoke detector of claim 1, further comprising a reducing element in the air path between the intake fan and the optical sensing unit, the reducing element configured to inhibit movement certain particulate matter from entering the optical sensing unit.

5. The active sampling smoke detector of claim 1, further comprising a dust collection chamber in the air path between the optical sensing unit and an access port in a housing of the smoke detector.

6. The active sampling smoke detector of claim 1, further comprising an exhaust hood on a door of the smoke detector, the exhaust hood configured to funnel exhaust air from the optical sensing unit outside of the housing to prevent contamination of the smoke detector from the surrounding environment.

7. The active sampling smoke detector of claim 1, wherein the optical sensing unit includes two detectors and a light source, a first detector being situated in line with the light source to provide an obscuration measurement of air flowing through the optical sensing unit and a second detector being situated perpendicular to the light source to provide a reflection measurement.

8. The active sampling smoke detector of claim 7, wherein the two detectors are configured to detect reflection of light off of particles in the air path that are 90 degrees of the light source and obscuration of light from the particles that are 180 degrees of the light source.

9. The active sampling smoke detector of claim 7, wherein the two detectors are infrared phototransistors and the light source is an infra-red light emitting diode.

10. The active sampling smoke detector of claim 7, wherein the optical chamber module further includes an optical filter between the light source and at least one of the two detectors to reduce an intensity of light received by at least one of the detectors.

11. The active sampling smoke detector of claim 1, wherein the optical chamber module further includes an air reducing path formed by side walls of the optical chamber module to prevent smoke in the air path from traveling above or below a light path between the light source and at least one of the detectors.

12. The active sampling smoke detector of claim 11, wherein the air reducing path is contiguous with the air path and forms an opening in the optical chamber module smaller than the air path.

13. A method of actively sampling for smoke in dusty conditions, comprising:
periodically activating an intake fan of a smoke detector to provide an air sample into an air path of a smoke detector;
directing the air sample through the air path and between a light emitter and two sensors in an optical sensing unit that detects smoke particles;
reducing an air space through which the air sample passes prior to the air sample passing between the light emitter and the two sensors in the optical sensing unit;
calculating an amount of obscuration of light from the emitter; and
determining if a fire exists based on the calculated amount of obscuration.

14. The method of claim 13, wherein providing the flow of air includes providing the flow of air through a u-shaped air path.

15. The method of claim 13, wherein directing includes directing the flow of air between the emitter and the two sensors and a first sensor is arranged in line with the emitter and a second sensor is perpendicular to the first sensor.

16. The method of claim 13, wherein providing includes controlling an intake fan over a sampling period based on instructions received from a controller of the smoke detector.

17. The active sampling smoke detector of claim 2, wherein the u-shaped air path is downstream of the intake fan and upstream of the optical sensing unit.

* * * * *